(12) United States Patent
McBride

(10) Patent No.: US 10,427,002 B2
(45) Date of Patent: Oct. 1, 2019

(54) METHODS AND APPARATUS FOR BALANCE SUPPORT SYSTEMS

(71) Applicant: Bioness Inc., Valencia, CA (US)

(72) Inventor: Keith McBride, Ventura, CA (US)

(73) Assignee: Bioness Inc., Valencia, CA (US)

( * ) Notice: Subject to any disclaimer, the term of this patent is extended or adjusted under 35 U.S.C. 154(b) by 650 days.

(21) Appl. No.: 15/013,277

(22) Filed: Feb. 2, 2016

(65) Prior Publication Data

US 2016/0220869 A1    Aug. 4, 2016

Related U.S. Application Data

(60) Provisional application No. 62/111,433, filed on Feb. 3, 2015.

(51) Int. Cl.
  *A63B 26/00*    (2006.01)
  *G05B 15/02*    (2006.01)
  (Continued)

(52) U.S. Cl.
  CPC .......... *A63B 26/003* (2013.01); *A63B 21/008* (2013.01); *A63B 22/18* (2013.01);
  (Continued)

(58) Field of Classification Search
  None
  See application file for complete search history.

(56) References Cited

U.S. PATENT DOCUMENTS 5,919,150 A * 7/1999 Zanakis ............... A61B 5/1036
                                                  600/595
6,036,046 A    5/2000 Allum
        (Continued)

FOREIGN PATENT DOCUMENTS

| DE | 102012108957 B3 | 9/2013 |
|---|---|---|
| EP | 0862930 A1 | 9/1998 |
| WO | WO 2016/126679 | 8/2016 |

OTHER PUBLICATIONS

International Search Report and Written Opinion for International Application No. PCT/US2016/016129, dated Jun. 2, 2016, 11 pages.
(Continued)

*Primary Examiner* — Sundhara M Ganesan
(74) *Attorney, Agent, or Firm* — Cooley LLP

(57) ABSTRACT

An apparatus includes a plate configured to support a user standing thereon, a set of fluid chambers configured to support at least a portion of the plate, and an electronic assembly in communication with at least one sensor. The sensor configured to sense a first operating condition associated with at least one of the set of fluid chambers and the plate. The electronic assembly is configured to define a second operating condition based at least in part on a difference between the first operating condition and a predetermined operating condition. The electronic assembly is configured to send (1) a first signal operable to transition each fluid chamber from a first configuration, associated with the first operating condition, to a second configuration, associated with the second operating condition, and (2) a second signal operable to graphically represent data associated with the second operating condition on a display of an electronic device.

20 Claims, 9 Drawing Sheets

(51) Int. Cl.
| | |
|---|---|
| *F16M 11/22* | (2006.01) |
| *A63B 71/06* | (2006.01) |
| *A63B 21/008* | (2006.01) |
| *A63B 22/18* | (2006.01) |
| *A63B 24/00* | (2006.01) |
| *G09B 19/00* | (2006.01) |
| *G16H 20/30* | (2018.01) |
| *A61B 5/11* | (2006.01) |
| *A63B 21/068* | (2006.01) |
| *A63B 22/00* | (2006.01) |
| *A63B 21/00* | (2006.01) |
| *A61B 5/00* | (2006.01) |

(52) U.S. Cl.
CPC ...... *A63B 24/0087* (2013.01); *A63B 71/0622* (2013.01); *F16M 11/22* (2013.01); *G05B 15/02* (2013.01); *G09B 19/0038* (2013.01); *G16H 20/30* (2018.01); *A61B 5/11* (2013.01); *A61B 5/4023* (2013.01); *A63B 21/0085* (2013.01); *A63B 21/068* (2013.01); *A63B 21/4034* (2015.10); *A63B 2022/0092* (2013.01); *A63B 2024/0093* (2013.01); *A63B 2071/065* (2013.01); *A63B 2071/0652* (2013.01); *A63B 2220/13* (2013.01); *A63B 2220/30* (2013.01); *A63B 2220/40* (2013.01); *A63B 2220/806* (2013.01); *A63B 2225/20* (2013.01); *A63B 2225/50* (2013.01); *F16M 2200/08* (2013.01)

(56) References Cited

U.S. PATENT DOCUMENTS

| | | | |
|---|---|---|---|
| 2003/0199374 A1* | 10/2003 | Perry | A61H 1/005 482/146 |
| 2005/0209049 A1* | 9/2005 | Shields | A61H 1/001 482/8 |
| 2006/0206175 A1* | 9/2006 | Fernandez Tournier | A63B 26/003 607/88 |
| 2007/0184953 A1* | 8/2007 | Luberski | A63B 22/18 482/146 |
| 2008/0280740 A1* | 11/2008 | Knecht | A61B 3/113 482/146 |
| 2008/0287263 A1 | 11/2008 | Cheng | |
| 2009/0303179 A1* | 12/2009 | Overholt | A63B 22/14 345/156 |
| 2013/0203571 A1* | 8/2013 | Kwon | A61H 1/0237 482/145 |
| 2015/0238816 A1* | 8/2015 | Naderer | A63B 22/16 482/4 |
| 2015/0343266 A1* | 12/2015 | Vardy | A61B 5/4023 482/8 |
| 2016/0256737 A1* | 9/2016 | Yoshioka | A63B 23/0405 |

OTHER PUBLICATIONS

Extended European Search Report for European Application No. 16747095.4, dated Sep. 3, 2018, 8 pages.

* cited by examiner

METHODS AND APPARATUS FOR BALANCE SUPPORT SYSTEMS

CROSS-REFERENCE TO RELATED APPLICATIONS

This application claims priority to and the benefit of U.S. Provisional Patent Application Ser. No. 62/111,433 entitled, "Methods and Apparatus for Balance Support Systems," filed Feb 3, 2015, the disclosure of which is incorporated herein by reference in its entirety.

BACKGROUND

The embodiments described herein relate generally to stability control and more particularly, to methods and apparatus for balance support, balance training, and/or balance assessment systems.

Successfully delivering intensive yet safe gait and/or balance training or therapy to individuals can present challenges. For example, in some instances, acute stages of neurological injuries such as stroke, spinal cord injury, traumatic brain injury, or the like can result in significant walking and/or balance deficits for some people. Such individuals often exhibit highly unstable walking patterns and poor endurance, making it difficult to safely practice gait for both the patient and therapist. In addition, these individuals often exhibit difficulty in establishing or re-establishing his or her sense of balance. Conversely, in some instances, it can be desirable to improve balance and/or coordination abilities in unimpaired individuals. For example, in some instances, gait, balance, and/or coordination training in athletes or the like can increase his or her performance.

Thus, a need exists for methods and apparatus for balance support, training, and/or assessment systems (also referred to herein as "balance support system").

SUMMARY

Apparatus and methods for balance systems are described herein. In some embodiments, an apparatus includes a plate configured to support a user standing thereon, a set of fluid chambers configured to support at least a portion of the plate, and an electronic assembly in communication with at least one sensor. The sensor configured to sense a first operating condition associated with at least one of the set of fluid chambers and the plate. The electronic assembly is configured to define a second operating condition based at least in part on a difference between the first operating condition and a predetermined operating condition associated with at least one of the set of fluid chambers and the plate. The electronic assembly is configured to send (1) a first signal operable to transition each fluid chamber from a first configuration, associated with the first operating condition, to a second configuration, associated with the second operating condition, and (2) a second signal operable to graphically represent data associated with the second operating condition on a display of an electronic device.

DETAILED DESCRIPTION

Figure 1:
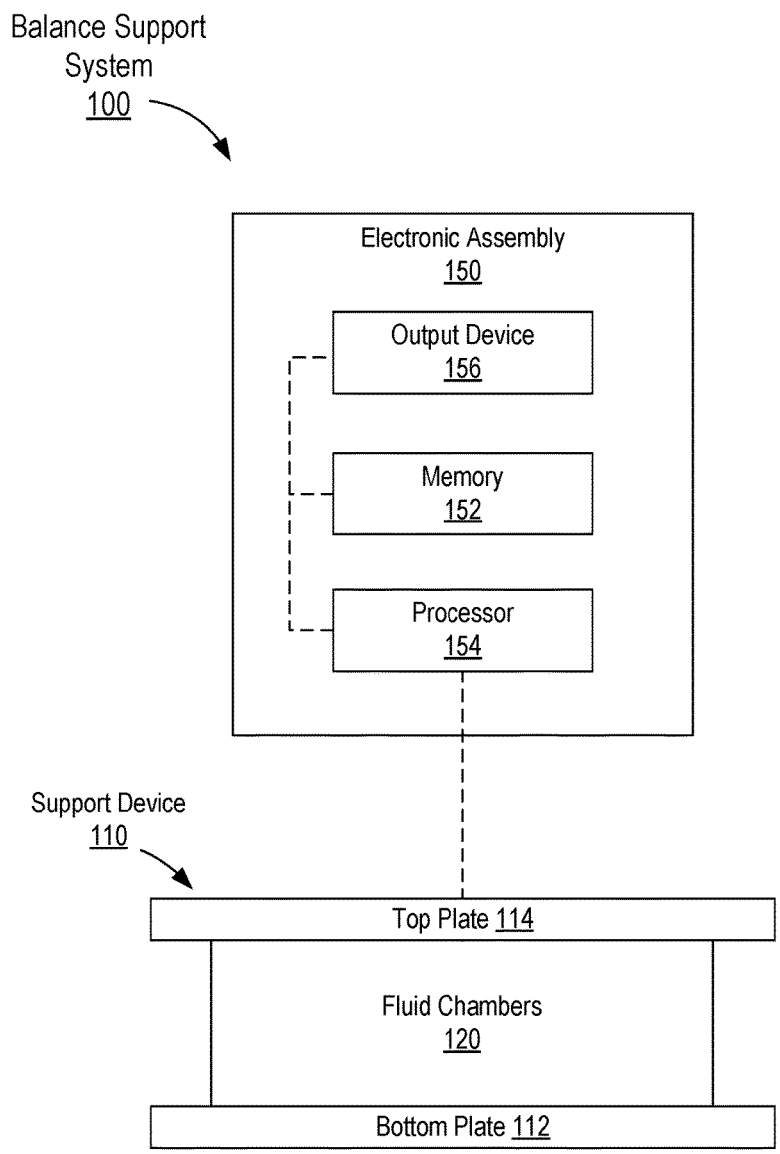
FIG. 1 is a schematic illustration of a balance support system according to an embodiment.

In some embodiments, an apparatus includes a plate configured to support a user standing thereon, a set of fluid chambers configured to support at least a portion of the plate, and an electronic assembly in communication with at least one sensor. The sensor configured to sense a first operating condition associated with at least one of the set of fluid chambers and the plate. The electronic assembly is configured to define a second operating condition based at least in part on a difference between the first operating condition and a predetermined operating condition associated with at least one of the set of fluid chambers and the plate. The electronic assembly is configured to send (1) a first signal operable to transition each fluid chamber from a first configuration, associated with the first operating condition, to a second configuration, associated with the second operating condition, and (2) a second signal operable to graphically represent data associated with the second operating condition on a display of an electronic device.

In some embodiments, a method includes sending, from a processor and to a display, a signal indicative of an instruction to graphically represent data associated with a predetermined coordinate along a plane on the display. The predetermined coordinate along the plane is based at least in part on a predetermined operating condition of a balance support device. The processor receives, from a sensor, a signal associated with a current operating condition of the balance support device. The current operating condition is based at least in part on a force exerted by a user standing on the balance support device. A coordinate along the plane based at least in part on the current operating condition of the balance support device is defined. Having defined the coordinate based at least in part on the current operating condition of the balance support device, a signal is sent from the processor the display. The signal is indicative of an instruction to graphically represent data associated with the coordinate and the data associated with the predetermined coordinate on the display.

In some embodiments, a method includes sending, from a processor and to a display, a signal indicative of an instruction to graphically represent data associated with a first predetermined coordinate along a plane on the display. The first predetermined coordinate along the plane is based at least in part on a first predetermined operating condition of a balance support device. The processor receives, for a sensor, a signal associated with a current operating condition of a balance support device. The current operating condition of the balance support device is based at least in part on a force exerted by a user standing on the balance support device. A current coordinate along the plane based at least in part on the current operating condition of the balance support device is defined. The processor sends, to the display, a signal indicative of an instruction to graphically represent an indication on the display when the current coordinate satisfies a criterion. A second predetermined coordinate along the plane is then defined. The second predetermined coordinate along the plane is based at least in part on a second predetermined operating condition of the balance support device that is different from the first predetermined operating condition of the balance support device.

As used in this specification, the singular forms "a," "an" and "the" include plural referents unless the context clearly dictates otherwise. Thus, for example, the term "a system" is intended to mean a single system or a combination of systems.

As used herein, the term "set" can refer to multiple features or a singular feature with multiple parts. For example, when referring to a set of chambers, the set of chambers can be considered as one chamber with multiple portions, or the set of chambers can be considered as multiple, distinct chambers (e.g., independently formed). Thus, a monolithically constructed item can include a set of chambers. Such a set of chambers may include multiple portions that are either continuous or discontinuous from each other. A set of chambers can also be fabricated from multiple items that are produced separately and are later joined together (e.g., via any suitable method).

As used herein the term "module" refers to any assembly and/or set of operatively-coupled electrical components that can include, for example, a memory, a processor, electrical traces, optical connectors, software (executing in hardware), and/or the like. For example, a module executed in the processor can be any combination of hardware-based module (e.g., a field-programmable gate array (FPGA), an application specific integrated circuit (ASIC), a digital signal processor (DSP)) and/or software-based module (e.g., a module of computer code stored in memory and/or executed at the processor) capable of performing one or more specific functions associated with that module.

FIG. 1 is a schematic illustration of a balance support system 100 according to an embodiment. The balance support system 100 includes a support device 110 and an electronic assembly 150 in communication with the support device 110. The balance support system 100 can be used, for example, during balance and/or coordination therapy and/or training. More specifically, a user seeking therapy and/or training (e.g., an individual with balance and/or coordination impairment or an unimpaired individual seeking to improve his or her balance and/or coordination) can stand on the support device 110 and based on a force exerted by the user, the electronic assembly 150 can control one or more operating conditions of the support device 110. Such operating conditions can include, for example, a magnitude and/or direction of a reaction force, an angle or tilt of a portion of the support device 110 on which the user stands, an operating state of one or more components, and/or the like. In some instances, the electronic device 150 can store therapy and/or training exercises, programs, routines, and/or instructions. In such instances, a user can stand on the support device 110 and can select a desired program and/or can otherwise interact with the electronic device 150 such that the desired program is initiated. In response, the electronic device 150 can control any suitable portion of the support device 110 to, for example, move, rotate, pivot, manipulate, and/or otherwise reconfigure the support device 110. In some instances, the reconfiguring of the support device 110 can result in a change in the user's sense of stability while standing on the support device 110. Thus, the balance support system 100 can provide balance and/or coordination therapy or training to the user standing on the support device 110.

As shown in FIG. 1, the support device 110 includes at least a first plate 112, a second plate 114, and a set of adjustable fluid chambers 120. The first plate 112 (also referred to herein as "bottom plate") and the second plate 114 (also referred to herein as "top plate") can be any suitable shape, size, and/or configuration. For example, in some embodiments, the bottom plate 112 and the top plate 114 can be formed from a relatively thin sheet or plate-like material (e.g., sheet metal, composite material, wood, etc.). In some embodiments, the bottom plate 112 and the top plate 114 are substantially similar. In other embodiments, the bottom plate 112 can have a first size or first shape and the top plate 114 can have a second size or second shape different from the first size or first shape, respectively. In still other embodiments, the support device 110 need not include the bottom plate 112. In such embodiments, any suitable portion of the support device 110, for example, can be positioned on the floor and/or the like.

The bottom plate 112 and the top plate 114 are separated by a distance with the set of fluid chambers 120 disposed therebetween. The set of fluid chambers 120 is configured to dynamically support the top plate 114 on which a user stands. The set of fluid chambers 120 can include any number of fluid chambers in any suitable arrangement. For example, in some embodiments, the set of fluid chambers 120 can include one fluid chamber, two fluid chambers, three fluid chambers, four fluid chambers, five fluid chambers, six fluid chambers, seven fluid chambers, eight fluid chambers, nine fluid chambers, ten fluid chambers, or more. Moreover, each fluid chamber in the set of fluid chambers 120 can be disposed in any suitable position relative to the bottom plate 112 and top plate 114. For example, in some embodiments, each fluid chamber 120 can be disposed at a different position at or near a perimeter of the bottom plate 112 and/or the top plate 114.

Each fluid chamber 120 in the set of fluid chambers 120 can be any suitable configuration. For example, in some embodiments, each fluid chamber 120 is a pneumatic and/or hydraulic spring or the like. More specifically, each fluid chamber 120 can include a flexible bellows or the like that defines an inner volume configured to receive a compressed gas and/or other suitable fluid. The fluid chambers 120 are each coupled to a compressor or fluid pump (at least partially controlled by the electronic assembly 150) configured to deliver a compressed gas and/or fluid to and/or receive a compressed gas and/or fluid from the inner volume of each fluid chamber to, for example, increase or decrease a volume within the inner volume. In other words, the inner volume defined by each fluid chamber 120 can receive a fluid (e.g., a liquid or a compressed gas) to increase a fluid pressure within the fluid chamber 120 or can expel the fluid to decrease the fluid pressure within the fluid chamber 120. Thus, by disposing the set of fluid chambers 120 between the bottom pate 112 and the top plate 114, a force exerted on the top plate 114 (e.g., associated with a user standing on the top plate 114) results in a predetermined and/or predictable deflection of one or more portions of each fluid chamber 120 and/or a change in pressure in each fluid chamber 120, which in turn, allows the top plate 114 to move relative to the bottom plate 112 in a predetermined and/or predictable motion. In embodiments where the support device 110 does not include the bottom plate 112, the deflection and/or change in pressure in each fluid chamber 120 can result in movement of the top plate 114 relative to a reference plane or the like (e.g., a plane otherwise parallel to the bottom plate 112).

Although not shown in FIG. 1, in some embodiments, the balance support system 100 can include any suitable control system configured to control and/or change an operating condition of the set of fluid chambers 120. For example, such as control system can include one or more mechanical stabilizers, springs, dampers, fluid pumps, compressors, actuators, etc. In such embodiments, the control system can be in communication with the electronic assembly 150 which can send signals to and/or receive signals from the control system. Thus, the electronic assembly 150 can control the operating condition of the control system and the set of fluid chambers 120 based on information or data received and/or determined by the electronic assembly 150, as described in further detail herein.

The electronic assembly 150 can be any suitable device or combination of devices. For example, in some embodiments, the electronic assembly 150 can be, for example, a personal computer (PC), a server device, a workstation, a controller, logic device, a personal digital assistant (PDA), a smartphone, a laptop, a tablet PC, and/or the like. In some embodiments, the system 100 can include more than one electronic assembly 150 each of which can control a portion of the system 100. For example, in some embodiments, the system 100 can include a first electronic assembly 150, which can be a controller or logic device included in the support device 110 and/or controlled by a therapist or trainer, and a second electronic assembly 150, which can be a personal electronic device such as a smartphone controlled by the patient and/or user. In such embodiments, each electronic assembly 150 can control a portion of the system 100 and/or can be configured to present data associated with the system 100 to the user, patient, therapist, trainer, etc.

The electronic assembly 150 includes at least a memory 152, a processor 154, and an output device 156. The memory 152 can be, for example, a random access memory (RAM), a memory buffer, a hard drive, a read-only memory (ROM), an erasable programmable read-only memory (EPROM), and/or the like. The memory 152 can be configured to store instructions, code, and/or modules associated with the system 100, which are executed by the processor 154. In some embodiments, the memory 152 can include and/or can otherwise be coupled to a database configured to store data associated with the system 100. Such a database, for example, can be a table, a repository, a relational database, an object-oriented database, an object-relational database, a structured query language (SQL) database, an extensible markup language (XML) database, and/or the like. In some embodiments, such a database can store data associated with, for example, predetermined operating conditions, historical operating conditions, user profiles, etc.

The processor 154 can be any suitable processing device configured to run or execute a set of instructions, code, and/or modules, for example, stored in the memory 152. The processor 154 can be a general-purpose processor, a central processing unit (CPU), an accelerated processing unit (APU), and Application Specific Integrated Circuit (ASIC), and/or the like. The processor 154 can be configured to run or execute a set of instructions, code, and/or modules stored in the memory 152 associated with, for example, a PC application, a mobile application, a network communication, a control system including one or more sensors, a programmable logic device (PLD), a proportional-integral-derivative (PID) control, and/or the like. For example, the processor 154 can be in communication the control system of the support device 110 and can be configured to run and/or execute a set of instructions stored in the memory 152 associated with operating the control system. In addition, the processor 154 can include and/or can be configured to execute one or more modules associated with querying the database, updating the database, and/or otherwise storing and retrieving data from the database.

The output device 156 can be any suitable output device or the like. For example, in some embodiments, the output device 156 is a display that can provide at least a portion of a user interface for a software application stored in the memory 152 and/or executed by the processor 154. In such embodiments, the output device 156 can be, for example, a cathode ray tube (CRT) monitor, a liquid crystal display (LCD) monitor, a light emitting diode (LED) monitor, and/or the like. In some embodiments, the output device 156 can be a touchscreen display. In other embodiments, an output device can be an audio device, a haptic device, and/or any other suitable output device.

Although not shown in FIG. 1, the electronic assembly 150 can include a communication interface configured to place the electronic assembly 150 in communication with any suitable electronic device (e.g., an external device or the like). The communication interface can be, for example, a peripheral port such as a Universal Serial Bus (USB) port, a network interface card and/or the like that can include at least an Ethernet port and/or a wireless radio (e.g., a WiFi® radio, a Bluetooth® radio, etc.), a Serial ATA (SATA) port, and/or any other suitable communication interface. Moreover, the processor 154 can include and/or can execute one or more modules and/or instructions associated with sending signal to and/or receiving signals from the communication interface. By way of example, the control system (described above) can be configured to send signals to and/or receive signals from the communication interface, which in turn, can send signals to and/or receive signals from the processor 154 or the like. In this manner, the processor 154 can execute a set of instructions stored in the memory 152 associated with controlling the control system.

In some embodiments, the processor 154 of the electronic assembly 150 can execute one or more processes, modules, routines, instructions, etc. associated with controlling one or more operating conditions of the support device 110. As described above, the electronic assembly 150 can receive one or more signals from a sensor such as, for example, a position sensor, a gyroscope, an accelerometer, an inclinometer, a tilt sensor, a pressure sensor, a strain gauge, a magnetic sensor, a distance sensor, and/or the like, and based on one or more current operating conditions of the support device 110 (e.g., a fill volume of the set of fluid chambers 120, a pressure within the set of fluid chambers 120, and/or a position, velocity, acceleration, or orientation of the top plate 114 relative to the bottom plate 112) can determine a difference between the current operating conditions of the support device 110 and a predetermined operating condition (e.g., stored as data in the memory). Moreover, when the difference between the current operating conditions and the predetermined operating conditions satisfies a criterion (e.g., is within a predetermined tolerance or the like), the processor 154 of the electronic assembly 150 can define, for example, a future and/or target operating condition associated with the support device 110 and can send a signal to the control system 130 to cause the control system 130 to correspondingly adjust the operating conditions of the support device 110 (e.g., adjust the fill volume and/or pressure within the fluid chambers 120 and/or the like).

In some embodiments, the processor 154 of the electronic assembly 150 can be configured to execute a set of instructions or code stored in the memory 152 and associated with one or more tests, routines, exercises, processes, etc., which can be performed by and/or attempted by a user standing on the support device 110. For example, in some instances, the electronic assembly 150 can determine a user performance score based on a timed test and/or an accuracy test. In some instances, such a test can be a static test or the like, in which the support device 110 and more specifically, the top plate. In other instances, such a test can be a dynamic test or the like, in which the electronic assembly 150 changes one or more operating conditions associated with the support device 110 (e.g., via the control system) and in turn, senses a change in force exerted by the user balancing on the top plate 114. Thus, the balance support system 100 can provide balance therapy and/or training to an individual standing on the support device 110.

Although not shown in FIG. 1, in some embodiments, the electronic assembly 150 can optionally include a camera, video recorder, and/or any other suitable means of capturing one or more images. For example, in such embodiment, a camera capable of capturing still images (e.g., pictures) and/or video can capture one or more images or video clips of the user while the user is performing one or more tests, programs, and/or training exercises using the balance support system 100. In this manner, the user and/or a therapist or trainer can determine the user's performance during the test, program, and/or training exercise via visual inspection of one or more images and/or video clips of the user while performing the test, program, and/or training exercise.

Figure 2:
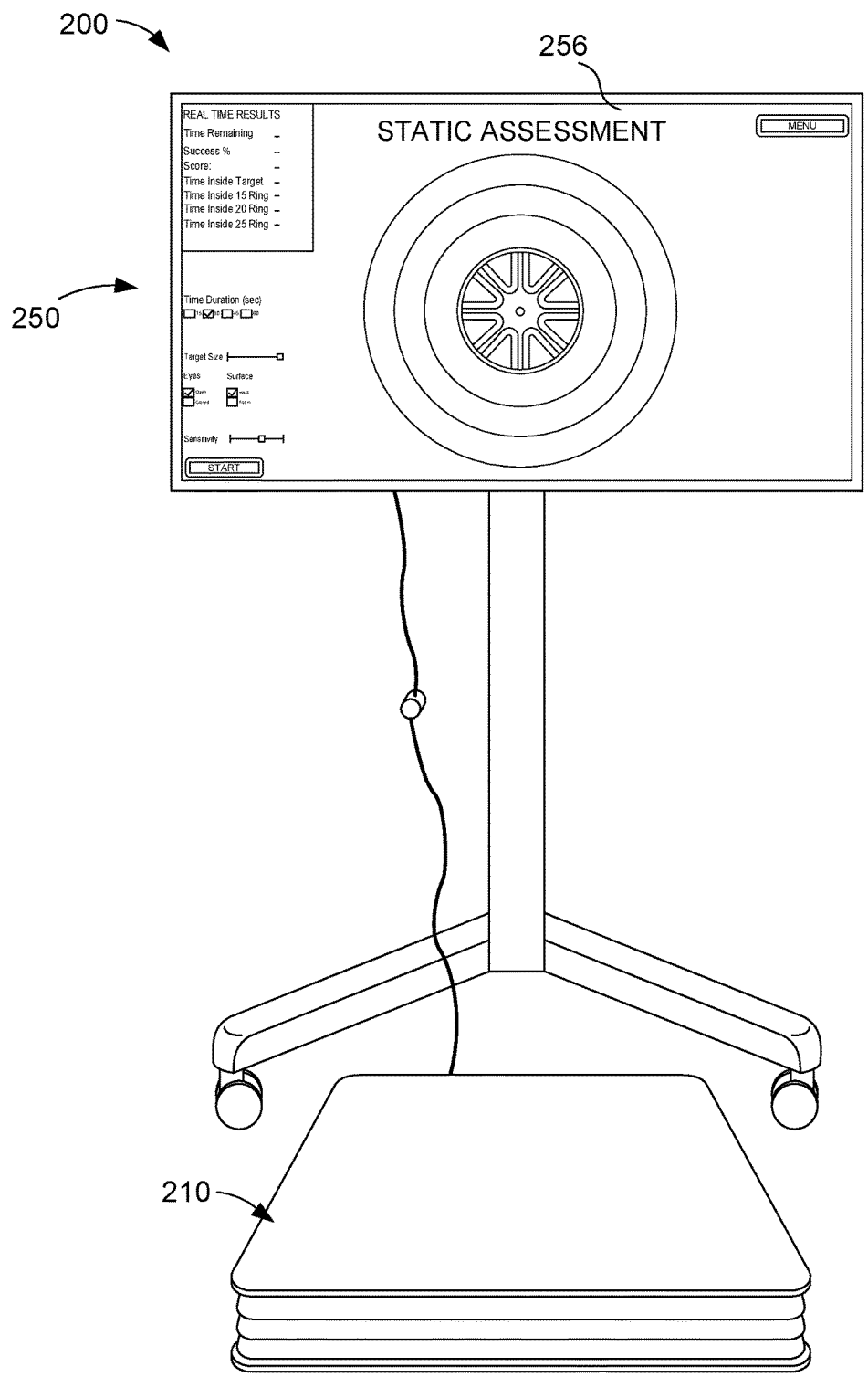
FIG. 2 is an illustration of a balance support system according to an embodiment.
Figure 3:
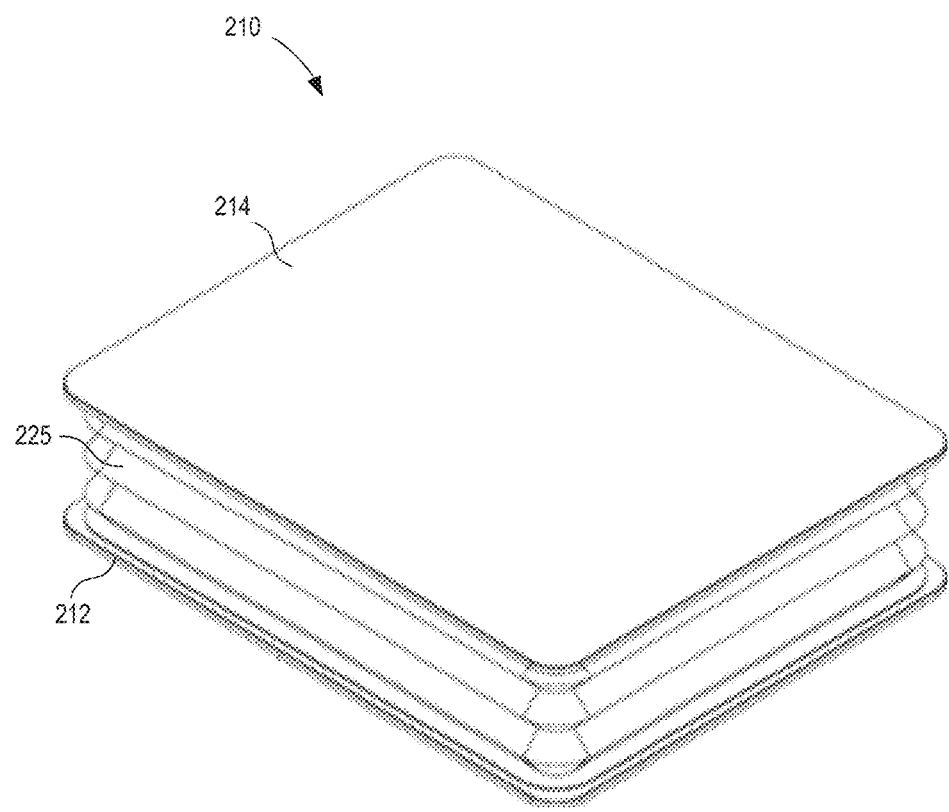
FIG. 3 is perspective view of a support device included in the balance support system of FIG. 1.
Figure 4:
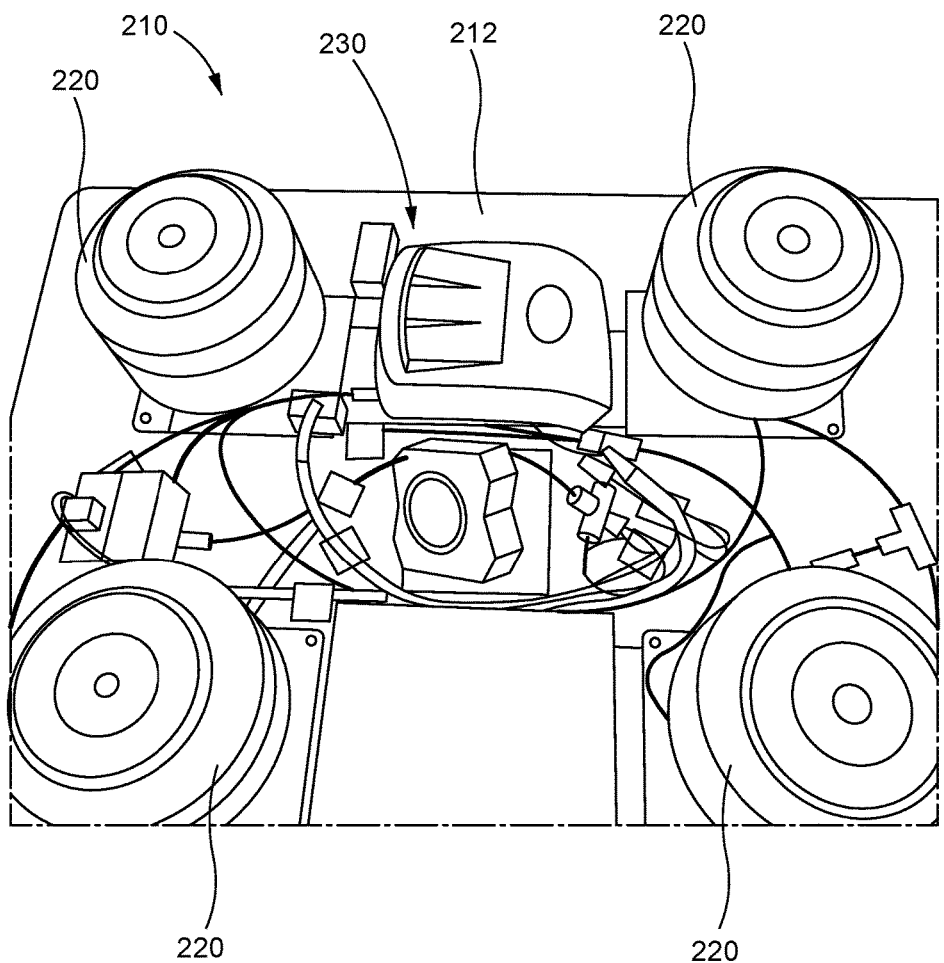
FIG. 4 is a top view of the support device of FIG. 2 shown without a top plate.

FIGS. 2-4 illustrate a balance support system 200 according to an embodiment. The balance support system 200 includes a support device 210 and an electronic assembly 250 (FIG. 2). The support device 210 includes a bottom plate 212, a top plate 214, a set of adjustable fluid chambers 220, a bellows 225, and an optional control system 230 (FIG. 4). The bottom plate 212 and the top plate 214 can be formed from a substantially flat plate-like material such as, for example, sheet metal, a composite plate, a wooden board (e.g., a board formed of a single piece of wood, plywood, particle board, medium density fiber (MDF), etc.), and/or the like. While the bottom plate 212 and the top plate 214 are shown in FIGS. 2-4, as being substantially rectangular, in other embodiments, the bottom plate 212 and the top plate 214 can have any suitable shape. For example, in some embodiments, the bottom plate 212 and the top plate 214 can be polygonal such as, for example, square, rectangular, pentagonal, hexagonal, heptagonal, octagonal, etc. In other embodiments, the bottom plate 212 and the top plate 214 can be rounded such as, for example, a circular, oblong, oval, ellipsoidal, elliptical, etc. In still other embodiments, the bottom plate 212 and/or the top plate 214 can have an asymmetrical and/or irregular shape.

While the bottom plate 212 and the top plate 214 are shown in FIGS. 2-4 as having substantially the same size and shape, in other embodiments, the support device 210 can include a bottom plate and a top plate that have different sizes and/or shapes. For example, in some embodiments, a bottom plate can be substantially rectangular while a top plate is octagonal (or any other polygonal shape other than rectangular. In other embodiments, a bottom plate can be polygonal while a top plate is substantially rounded (e.g., circular, oblong, etc.).

The set of fluid chambers 220 is disposed between the bottom plate 212 and the top plate 214 and is configured to dynamically support the top plate 214 on which a user stands. The set of fluid chambers 220 can be any suitable arrangement. For example, in this embodiment, the set of fluid chambers 220 includes four fluid chambers each of which is disposed at or near a different corner of the bottom plate 212 and/or top plate 214. In other embodiments, however, the support device 210 can include any suitable number of fluid chambers in any suitable arrangement.

Each fluid chamber 220 can be any suitable configuration. For example, in some embodiments, each fluid chamber 220 is a pneumatic and/or hydraulic spring or the like. More specifically, each fluid chamber 220 can include a flexible bellows or the like that defines an inner volume configured to receive a compressed gas and/or other suitable fluid. The fluid chambers are each coupled to a compressor or fluid pump configured to deliver a compressed gas and/or fluid to and/or receive a compressed gas and/or fluid from the inner volume of each fluid chamber to, for example, increase or decrease a volume within the inner volume. In other words, the inner volume defined by each fluid chamber 220 can receive a fluid (e.g., a liquid or a compressed gas) to increase a fluid pressure within the fluid chamber 220. As such, when an external force is exerted on a given fluid chamber 220 the fluid pressure within the inner volume exerts a reaction force in response thereto. In some instances, the external force can further compress the fluid within the fluid chamber 220 and/or can deform the flexible bellows forming a portion of the fluid chamber 220, which in turn, results in a predetermined deflection of one or more surfaces of the fluid chamber 220. Thus, by disposing the set of fluid chambers 220 between the bottom pate 212 and the top plate 214, a force exerted on the top plate 214 (e.g., associated with a user standing on the top plate 214) results in a predetermined and/or predictable deflection of one or more portions of each fluid chamber 220 and/or a change in pressure in each fluid chamber 220, which in turn, allows the top plate 214 to move relative to the bottom plate 212 in a predetermined and/or predictable motion.

As shown, for example, in FIG. 3, the bellows 225 is coupled to, for example, a perimeter portion of the bottom plate 212 and a perimeter portion of the top plate 214. The bellows 225 can be a flexible member configured to flex, bend, deform, and/or otherwise reconfigure in response to relative movement between the bottom plate 212 and the top plate 214. In this manner, the bellows 225 can be configured to isolate (e.g., physically and/or fluidically isolate) a volume within the bellows 225 from a volume outside of the bellows 225. In other words, the bellows 225 isolate a volume within the bellows 225 and between the bottom plate 212 and top plate 214 from a volume outside of the bellows 225. As shown in FIGS. 3-4, the set of fluid chambers 220 and at least a portion of the control system 230 are disposed between the bottom plate 212 and the top plate 214 and within the bellows 225 and thus, are isolated from a volume outside of the bellows 225.

Although not shown, in some embodiments, the control system 230 can include at least a power source, a mechanical stabilizer, a fluid pump, and one or more sensors. The power source can be any suitable alternating current (AC) power source (e.g., a wall socket or the like) or any suitable direct current (DC) power source (e.g., a battery). Thus, the power source can supply electrical power to the fluid pump, the one or more sensors, the electronic assembly 250, and/or any other portion of the balance support system. The optional mechanical stabilizer (not shown) can be any suitable stabilizer. In some embodiments, the mechanical stabilizer is positioned in the center of the support device 210 to mechanically connect the bottom plate 212 to the top plate 214, thereby increasing stability of the top plate 214 and allowing, for example, 2-axis rotation, such as U-joint.

The one or more sensors can be any suitable sensor such as, for example, a position sensor, a gyroscope, an accelerometer, an inclinometer, a tilt sensor, a pressure sensor, a strain gauge, a distance sensor, and/or the like. The one or more sensors are in communication with, for example, the control system 230 and/or the electronic assembly 250 via a wired or wireless connection, as described in further detail herein. The sensor senses the angle of the top plate 214 relative to the bottom plate 212 based at least in part on a position, velocity, acceleration, and/or orientation of the top plate 214 and/or one or more operating conditions associated with the adjustable fluid chambers 220 such as, for example, pressure, volume, force, and/or the like. In some embodiments, the sensor(s) can sense and/or determine an angle of the top plate 214 based on one or more calculations of data such as, for example, an integration of an angular velocity, and/or the like. In other embodiments, the position and/or angle of the top plate 214 can be calculated using linear acceleration data from any suitable number of sensors located at various positions on the top plate 214. Based on the angle of the top plate 214, the electronic assembly 250 and more specifically, the processor included therein, can determine if the user is stable within a predetermined range, as described in further detail herein, or it can track the user's spatial position (e.g., a 2-dimensional (2-D) angle), and the user's motion parameters.

In some embodiments, the fluid pump can be included in the control system 230 and can be in fluid communication with each fluid chamber 220. As described in further detail herein, the control system 230 can be configured to monitor, change, adjust, and/or otherwise control one or more operating conditions associated with the set of adjustable fluid chambers 220. For example, based at least in part on a current operating condition, the control system 230 can cause the fluid pump to increase or decrease a volume (or pressure) of fluid (e.g., air, oil, water, etc.) disposed in one or more of the fluid chambers 220, thereby increasing and/or decreasing a volume and/or pressure therein. In some instances, the fluid pump can be in communication with one or more valves that can selectively direct the flow of fluid from the fluid pump to one or more of the fluid chambers 220 (e.g., based at least in part on an operating condition sensed by the sensor, and/or manually adjusted by a user). Although shown in FIG. 4 as including four fluid chambers 220, in other embodiments, a support device can include any suitable number of fluid chambers in any suitable configuration. As described in further detail herein, the control system 230 can receive a signal from the sensor and/or from the electronic assembly 250 and based on data included in and/or represented by the signal, the fluid pump and/or the valves can increase and/or decrease a volume (or pressure) of fluid within one or more of the fluid chambers 220.

In some instances, the fluid pump (e.g., an air pump) and the valves can deliver substantially the same volume of fluid to each fluid chamber 220. In other instances, the fluid pump and the valves can selectively deliver fluid to a subset of the fluid chambers 220 (e.g., to one fluid chamber 220, to two fluid chambers 220, etc.) and/or a different volume of fluid to each fluid chamber 220. Moreover, the control system 230 can be configured to adjust and/or otherwise control the volume of fluid in each fluid chamber 220 in response to a user (e.g., a patient) standing on the top plate 214. In other words, the control system 230 can selectively adjust a volume of fluid within the fluid chambers 220 in response to a change in force and/or pressure exerted on the top plate 214 by the user. Thus, the support device 210 can facilitate and/or otherwise provide balance training, therapy, and/or the like of a user, as described in further detail herein.

The electronic assembly 250 can include and/or can be in communication with any suitable device or combination of devices. For example, in some embodiments, the electronic assembly 250 can include and/or can be in communication with a personal computer (PC), a personal digital assistant (PDA), a smartphone, a laptop, a tablet PC, a server device, a workstation, and/or the like. In some embodiments, the electronic assembly 250 can be included in the support device 210. In other embodiments, the electronic assembly 250 can be separate from the support device 210 and in communication with the support device 210 via a wired or wireless connection. In still other embodiments, a first portion of the electronic assembly 250 can be included in the support device 210 (e.g., the control system 230 and/or the like), while a second portion is separate from but in communication with the first portion. For example, in some embodiments, the system 200 can include a first electronic assembly 250, which can be a controller or logic device included in the support device 210 and/or controlled by a therapist or trainer, and a second electronic assembly 250, which can be a personal electronic device such as a smartphone controlled by the patient and/or user. In such embodiments, each electronic assembly 250 can control a portion of the system 200 and/or can be configured to present data associated with the system 200 to the user, patient, therapist, trainer, etc.

The electronic assembly 250 can include at least a memory, a processor, a communication interface, and an output device 256 (see e.g., FIG. 2). In some embodiments, the electronic assembly 250 can be substantially similar in form and/or function as the electronic assembly 150 described above with reference to FIG. 1. Thus, portions of the electronic assembly 250 are not described in further detail herein. The communication interface (not shown) can be, for example, a peripheral port such as a Universal Serial Bus (USB) port, a network interface card and/or the like that can include at least an Ethernet port and/or a wireless radio (e.g., a WiFi® radio, a Bluetooth® radio, etc.), a Serial ATA (SATA) port, and/or any other suitable communication interface. In some embodiments, the output device 256 can be a display that can provide at least a portion of a user interface for a software application stored in the memory and/or executed by the processor. In such embodiments, the display can be, for example, a cathode ray tube (CRT) monitor, a liquid crystal display (LCD) monitor, a light emitting diode (LED) monitor, and/or the like. More specifically, in this embodiment, the output device 256 can be a touchscreen display. In other embodiments, an output device can be an audio device, a haptic device, and/or any other suitable output device.

The memory (not shown) can be, for example, a random access memory (RAM), a memory buffer, a hard drive, a read-only memory (ROM), an erasable programmable read-only memory (EPROM), and/or the like. The memory can be configured to store instructions, code, and/or modules associated with the system 200. In some embodiments, the memory can include and/or can otherwise be coupled to a database configured to store data associated with the system 200. Such a database, for example, can be a table, a repository, a relational database, an object-oriented database, an object-relational database, a structured query language (SQL) database, an extensible markup language (XML) database, and/or the like.

The processor (not shown) can be any suitable processing device configured to run or execute a set of instructions, code, and/or modules, for example, stored in the memory. The processor can be a general-purpose processor, a CPU, an APU, an ASIC, and/or the like. The processor can be configured to run or execute a set of instructions, code, and/or modules stored in the memory associated with, for example, a PC application, a mobile application, a network communication, a control system including one or more sensors, a programmable logic control (PLC), a proportional-integral-derivative (PID) control and/or the like. For example, the processor can be in communication the control system 230 of the support device 210 and can be configured to run and/or execute a set of instructions associated with operating the control system 230, as described herein.

In some embodiments, the processor of the electronic assembly 250 can execute one or more processes, modules, routines, instructions, etc. associated with controlling one or more operating conditions of the support device 210. As described above, the electronic assembly 250 can receive one or more signals from the control system 230 (e.g., from a sensor included therein) and based on one or more current operating conditions of the support device 210 (e.g., a fill volume of the set of fluid chambers 220, a pressure within the set of fluid chambers 220, and/or a position, velocity, acceleration, or orientation of the top plate 214 relative to the bottom plate 212) can determine a difference between the current operating conditions of the support device 210 and a predetermined operating condition (e.g., stored as data in the memory). Moreover, based on the difference between the current operating conditions and the predetermined operating conditions, the electronic assembly 250 can define, for example, a future and/or target operating condition associated with the support device 210 and can send a signal to the control system 230 to cause the control system 230 to correspondingly adjust the operating conditions of the support device 210 (e.g., adjust the fill volume and/or pressure within the fluid chambers 220 and/or the like). In other words, when the difference between the current operating conditions and the predetermined operating conditions satisfies a criterion, the electronic assembly 250 can define the future and/or target operating condition. Such a criterion can be, for example, when the current operating conditions are substantially equal to the predetermined operating conditions (e.g., within a given or predetermined tolerance).

In some embodiments, the processor of the electronic assembly 250 can be configured to execute a set of instructions and/or modules stored in the memory to cause the output device 256 (e.g., the touchscreen display) to graphically represent data associated with the system 200, the user's performance, and/or any other suitable data such as one or more operating conditions of the support device 210. For example, the output device 256 can be configured to graphically represent data associated with any suitable operating condition of the support device 210 (e.g., a power state of the support device 210, a fill volume and/or pressure of the fluid chambers 220, a current angle and/or a desired angle of the top plate 214 relative to the bottom plate 212, and/or the like). In some embodiments, movement of the top plate 214 relative to the bottom plate 212 can result in a cursor and/or any other indicator being moved to various positions along the output device 256 (e.g., display). Said another way, the electronic assembly 250 can receive data associated with a current state or current operating condition of the support device 210 and based on the data, the processor can define a coordinate or the like along a plane (e.g., an X-Y plane or the like), which in turn, is graphically represented as the cursor and/or indicator on the output device 256 (e.g., display).

In some embodiments, the memory of the electronic assembly 250 can store instructions, code, and/or data associated with one or more tests, routines, exercises, processes, and/or the like. In addition, the processor of the electronic assembly 250 can be configured to determine a user's performance in taking and/or performing the one or more tests, routines, exercises, processes, etc. and can define a score or the like associated with the performance. For example, the electronic assembly 250 can determine a user performance score based on a timed test and/or an accuracy tests. Such tests and/or performance scores can be stored, for example, in the memory and/or in a database included in and/or operably coupled to the memory.

Figure 5:
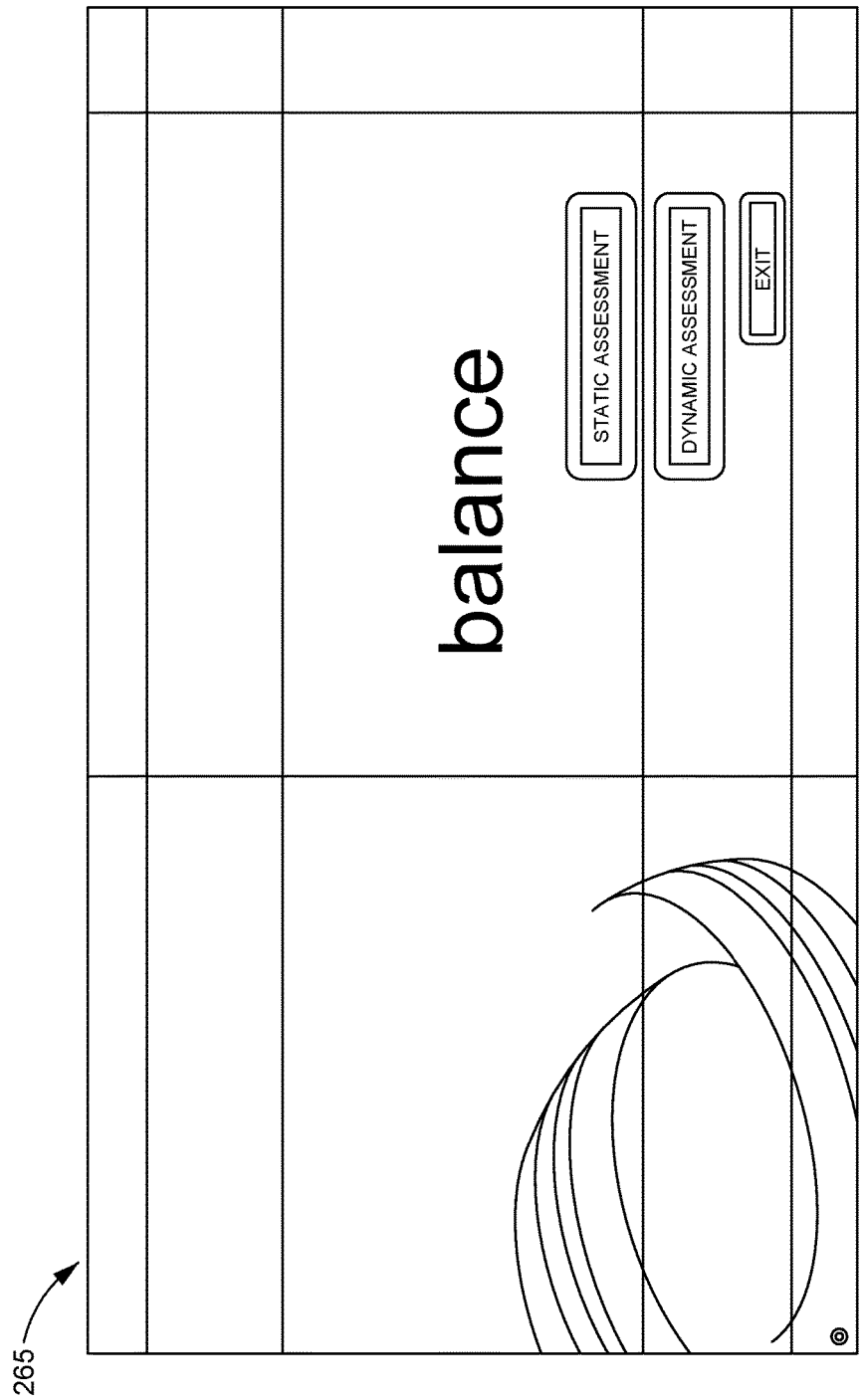
FIGS. 5-7 are each screenshots illustrating different portions of a balance support system each according to an embodiment.
Figure 6:
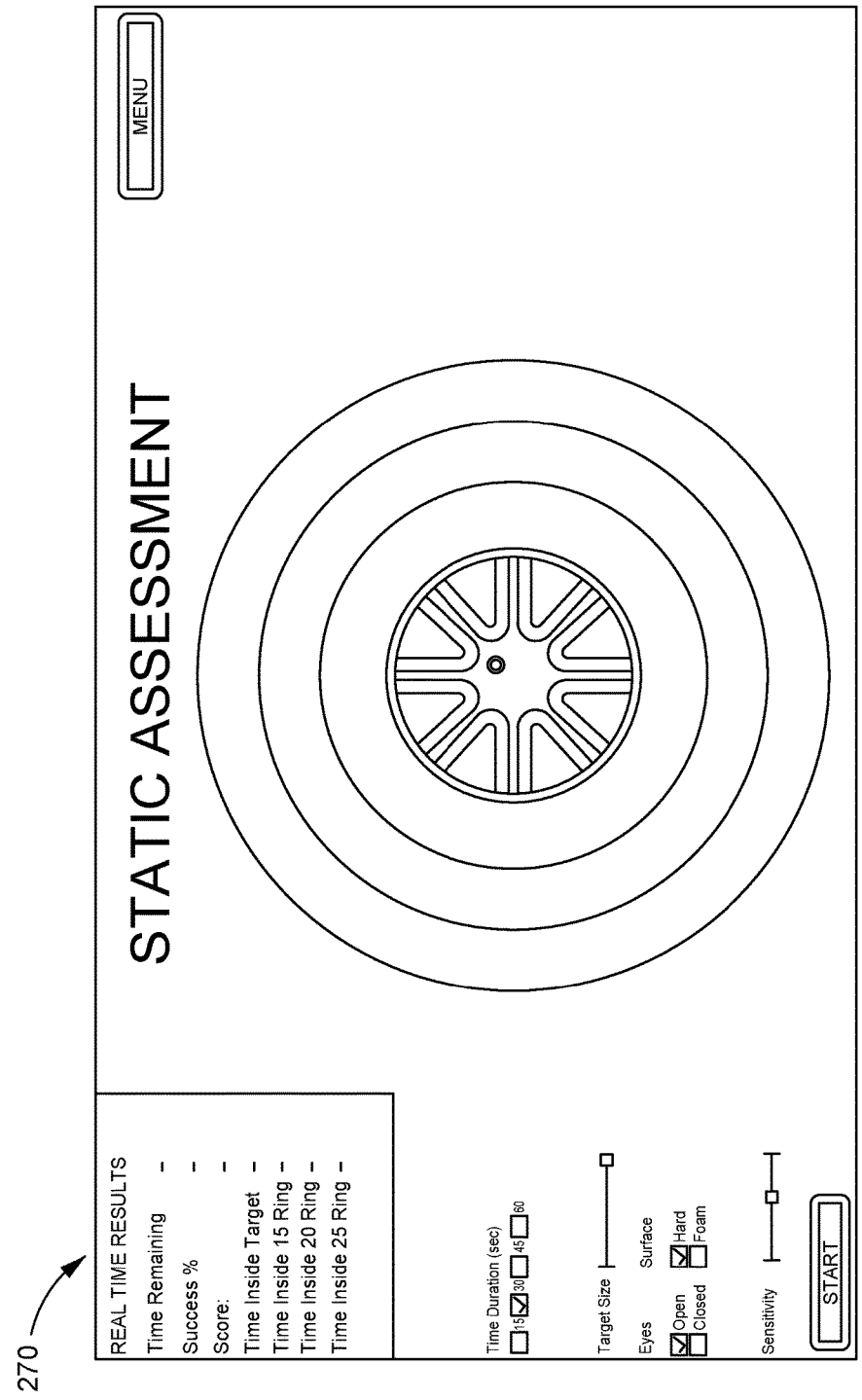

For example, FIG. 5 is a screenshot 265 of a touchscreen display (e.g., the output device 256) illustrating a home screen. In some instances, the user can select a predetermined assessment from the home screen (e.g., by pressing or tapping on a button, selecting from a drop down menu, and/or otherwise choosing from a selection graphically represented on the touchscreen display. For example, as illustrated by the screenshot 270 in FIG. 6, a user can select a "Static Assessment" and the processor of the electronic assembly 250 can execute a set of instructions to cause data associated with the "Static Assessment" to be graphically represented on the output device 256. In some embodiments, the data graphically represented on the output device 256 (e.g., the touchscreen device) can include, for example, adjustable parameters such as target size, target speed, target pattern, overall sensor sensitivity, sensor calibration (e.g., center the cursor and calibrate the anterior-posterior and lateral range of the motion), air pressure or volume within the fluid chambers 220 or adjustments thereof, and/or any other suitable parameter. In some embodiments, the Static Assessment can determine a user's ability to balance on the support device 210 while keeping the cursor within the targeted zone or the like. In addition, the electronic assembly 250 and more specifically, the processor can execute a set of instructions or code stored in the memory, which in turn, can cause the control system 230 to determine if the user is within, for example, a static target zone (e.g., when the user is substantially not moving). The electronic device 250 can determine one or more operating conditions associated with the support device 210 and can send a signal to the control system 230 to cause the control system 230 to correspondingly adjust the current operating conditions associated with the support device 210 (e.g., the fluid chambers 220) during the "Static Assessment."

Figure 7:
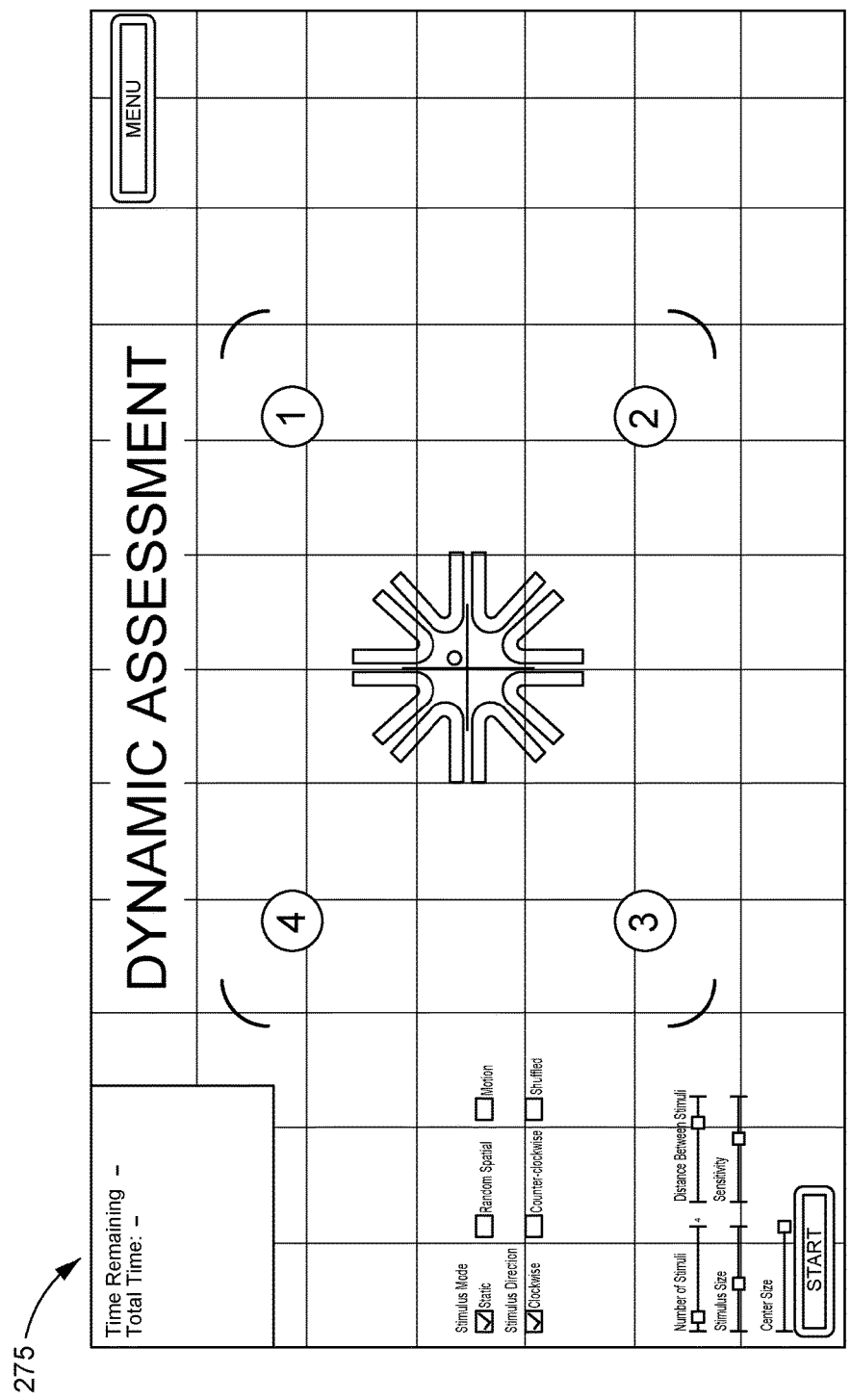

As illustrated by the screenshot 275 in FIG. 7, in other instances, a user can select a "Dynamic Assessment" and the processor of the electronic assembly 250 can execute a set of instructions to cause data associated with the "Dynamic Assessment" to be graphically represented on the output device 256 (e.g., the touchscreen display). In addition, the electronic assembly 250 and more specifically, the processor can execute a set of instructions or code stored in the memory, which in turn, can cause the control system 230 to determine if the user is accurately hitting and/or following a predetermined set of targets graphically represented on the output device 256. In some embodiments, the data presented on the output device 256 (e.g., the touchscreen device) can include, for example, adjustable parameters such as target size, target speed, target pattern, overall sensor sensitivity, air pressure or volume within the fluid chambers 220 or adjustments thereof. In some embodiments, the Dynamic Assessment can determine a user's ability to balance on the support device 210 while moving the cursor between the targets of different sizes, moving the cursor in a certain order or a random order, and/or tracking a moving target. Moreover, the electronic device 250 can determine one or more operating conditions associated with the support device 210 and can send a signal to the control system 230 to cause the control system 230 to correspondingly adjust the current operating conditions associated with the support device 210 (e.g., the fluid chambers 220) during the "Dynamic Assessment."

Although specifically described above, a balance support system can be any suitable configuration and can include any suitable device, mechanism, sensor, control, etc. configured to facilitate balance training and/or balance therapy of a patient. In some instances, a balance support device such as the support device 210 can be used in conjunction with other therapeutic programs graphically represented on, for example, a touch screen interface (e.g., the output device 256). As such, health care professionals can test and track a patient's balance while they are completing other touch screen visuomotor training exercises.

Although not described above, in some embodiments, a support device such as the support device 210 can include any suitable sensor and/or other device configured to determine one or more operating conditions associated with the support device. For example, in some embodiments, a support device can include a sensor mat or the like disposed on an outer surface of a top plate (e.g., the top plate 214). In some embodiments, a balance support system can include a camera and/or the like configured to capture images and/or video to provide, for example, motion data for a motion analysis. In some embodiments, a top plate can include different surfaces to promote balance training with varying levels of proprioceptive feedback (e.g., a foam overlay).

Figure 8:
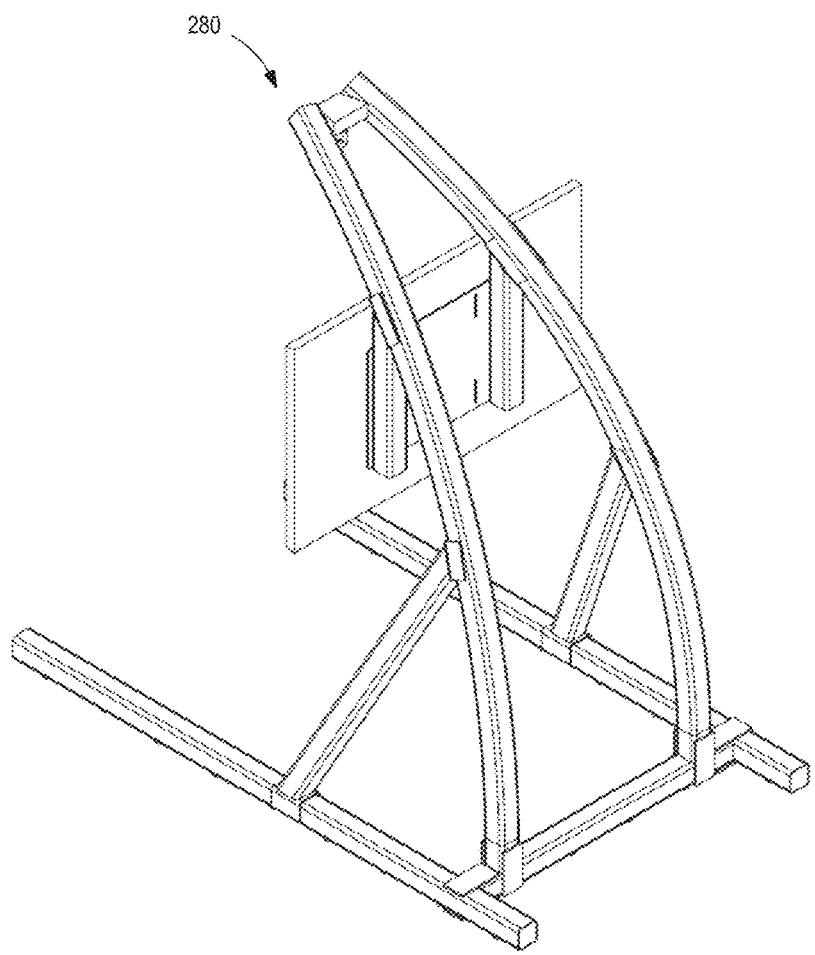
FIG. 8 is a portion of a therapy station according to an embodiment.

In some embodiments, a balance support system can be included in and/or can form a therapy station or the like. For example, FIG. 8 illustrates a frame 280 according to an embodiment, and configured to be used in conjunction with, for example, the support device 210 and the electronic device 250. In some instances, the frame 280 can include and/or can be used with a safety harness fixture and/or the like that can provide a patient with a desired range of motion to allow the user to interact with, for example, a touchscreen display while standing on and/or otherwise using a support device such as the support device 210.

Figure 9:
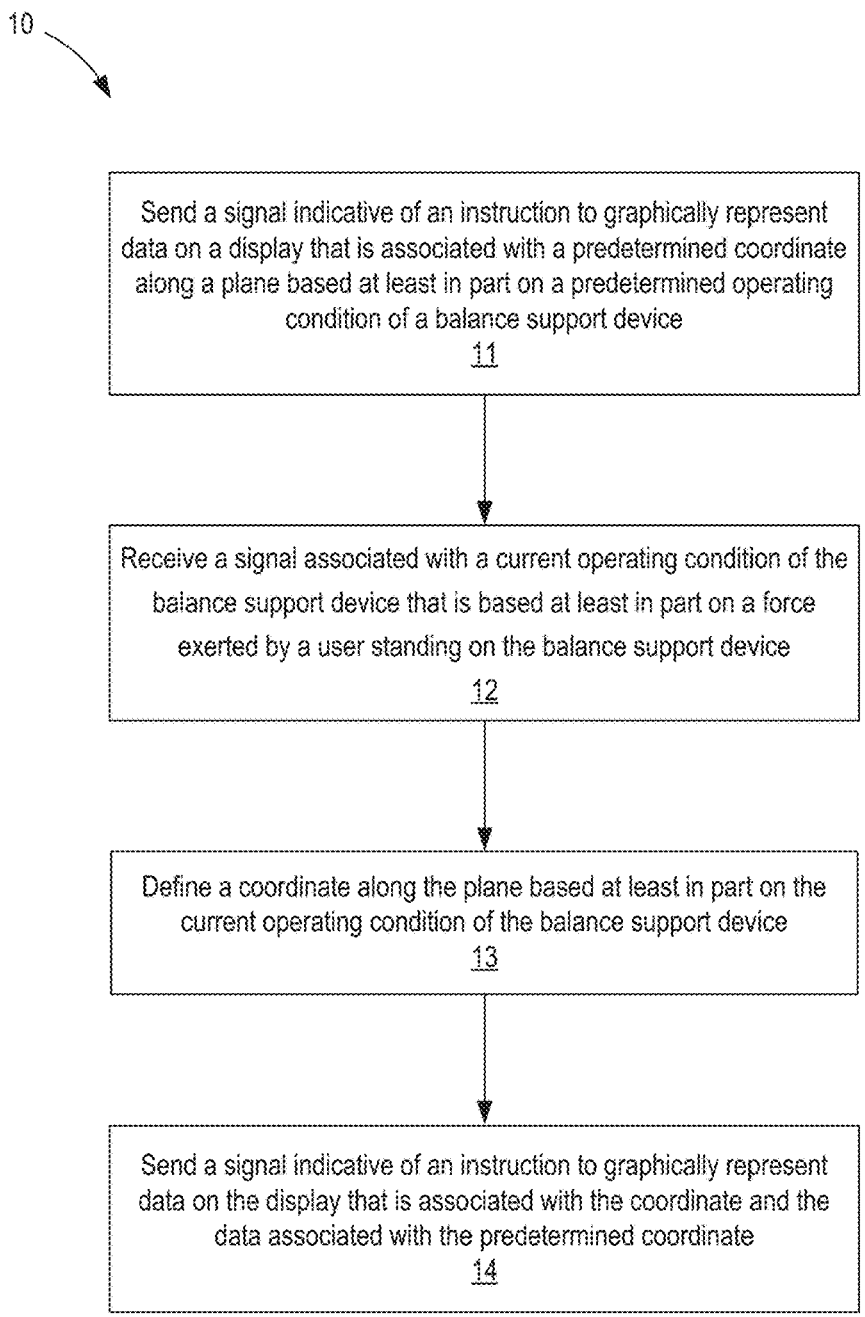
FIG. 9 is a flowchart illustrating a method of using a balance support system according to an embodiment.

Referring now to FIG. 9, a flowchart is shown illustrating a method 10 of using a balance support system according to an embodiment. The balance support system can be any suitable system such as, for example, the balance support system 100 described above with reference to FIG. 1, and/or the balance support system 200 described above with reference to FIGS. 2-8. As such, the balance support system can include a support device (e.g., the support device 210) in electronic communication with an electronic assembly (e.g., the electronic assembly 250). The support device can include, for example, a set of fluid chambers disposed between a first (e.g., top) plate and a second (e.g., bottom) plate. The first plate can be configured to move relative to the second plate in response to a change in operating condition of at least one fluid chamber such as, for example, a change in fluid pressure, fluid fill volume, etc., as described in detail above with reference to the support device 210. The support device can also include a control system or the like in electronic communication with the electronic assembly and in fluid communication with each fluid chamber from the set of fluid chambers. In this manner, the control system can receive signals from and/or can send signals to the electronic assembly associated with controlling an operating condition of the support device.

The method 10 includes sending a signal indicative of an instruction to graphically represent data on a display that is associated with a predetermined coordinate along a plane based at least in part on a predetermined operating condition of the support device, at 11. For example, as described above with reference to the balance support systems 100 and 200, the electronic assembly includes at least a processor, a memory, and a display. As such, the processor of the electronic assembly can execute a set of instructions or code stored in the memory to (1) define the predetermined operating condition and (2) send the signal to the display to graphically represent the data associated with the predetermined operating condition. More particularly, in this instance, the predetermined operating condition can be associated with, for example, a predetermined, target, and/or desired tilt of the first plate relative to the second plate. The predetermined coordinate, in turn, can correspond to a graphically represented position on the display. Thus, the electronic assembly correlates the predetermined operating condition to a predetermined position on the display. In some instances, the predetermined operating condition and/or the predetermined coordinate can be based at least in part on a user input. For example, a therapist and/or training can input data, and in response, the processor defines the predetermined operating condition and/or predetermined coordinate based at least in part on the data.

The electronic assembly (e.g., the processor) receives a signal associated with a current operating condition of the balance support device that is based at least in part on a force exerted by a user standing on the balance support device, at 12. For example, once the predetermined operating condition and/or the predetermined coordinate are defined and graphically represented on the display, a user (e.g., a patient or an individual seeking to receive balance and/or coordination therapy or training) can stand on the first plate. Thus, the force exerted by the user from standing on the first plate changes the operating condition of one or more of the fluid chambers, which in turn, can result in the first plate tilting relative to the second plate. A sensor or the like included in the control system and/or the electronic assembly can therefore, sense a change in the operating condition and can send a signal to the processor associated with the current operating condition.

The processor defines a coordinate along the plane based at least in part on the current operating condition of the balance support device, at 13. As described above with reference to the predetermined coordinate, the coordinate along the plane corresponds to and/or correlates to a position on the display. Therefore, the processor sends a signal indicative of an instruction to graphically represent data on the display that is associated with the coordinate and the data associated with the predetermined coordinate, at 14. Thus, the user and/or the therapist or trainer can visually compare the position of the coordinate graphically represented on the display to the position of the predetermined coordinate graphically represented on the display. Based at least in part on the comparison, the user and/or the therapist or trainer can determine the user's performance in placing the operating condition of the support device within a predetermined and/or desired tolerance relative to the predetermined operating condition.

In some instances, the method can optionally include defining a second predetermined coordinate along the plane when the current coordinate is within the predetermined and/or desired tolerance relative to the first predetermined coordinate. The second predetermined coordinate can be associated with a different position on the display and a different operating condition associated with the balance support device. As such, a user can adjust the way he or she is standing on the first plate of the balance support device, which in turn, changes the force exerted thereon. Thus, the user can change the current operating condition of the balance support device to bring the current operating condition within the predetermined and/or desired tolerance relative to, for example, the second predetermined operating condition. In this manner, the method 10 can be used in balance and/or coordination therapy and/or training by defining any suitable number of predetermined operating conditions, which a user, in turn, attempts to replicate by balancing and/or otherwise adjusting the force exerted on the first plate.

In some embodiments, a patient using a balance support system such as the support system 100 and/or 200 described herein can use one or more Functional Electrical Stimulators (either external or implanted) to mitigate challenges associated with conditions such as upper motor neuron injury or disease. For example, such a Functional Electrical Stimulator (FES) can be a NESS L300® stimulator, manufactured by Bioness, Inc., used to mitigate adverse effects of a foot drop condition. In some instances, using electrical stimulators can improve a patient's stability, range of motion, and/or the like. In some instances, it may be desirable to provide feedback from the balance support system to the FES system used by the patient (e.g., via a wireless communication or the like). The feedback can include data associated with, for example, a starting or stopping stimulation condition, a change in stimulation parameters and/or intensity, or stimulation timing in response to tilt, speed, or other parameters of the support device or in response to patient's performance for different tasks performed using the balance support system. Similarly, the FES system can be configured to provide data and/or feedback to the balance support system associated with one or more operating conditions of the FES system, one or more system or patient parameters, and/or the like. In some instances, a patient, therapist, and/or trainer can be configured to control at least a portion the FES system and/or the balance support system via an electronic device such as a smartphone or other controller (e.g., a device similar to the electronic assembly 150 and/or 250 described herein).

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™ Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, FORTRAN, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. For example, while the top plate 214 is shown and described above as being a single plate (e.g., a continuous plate having a substantially rectangular shape), in other embodiments, a support device can include, for example, a top plate having two independent portions (e.g., two top plates). In such embodiments, for example, a user can stand on a first top plate or first portion of the top plate with a first leg and can stand on a second top plate or second portion of the top plate with a second leg. In this manner, an electronic assembly and/or control system can be configured to independently control the first top plate (or first portion of the top plate) and the second top plate (or second portion of the top plate).

While the support device 210 is described above as including the set of fluid chambers 220 that are configured to dynamically support and/or move the top plate 214, in other embodiments, a support device can include any suitable mechanism configured to perform a substantially similar function. For example, in some embodiments, a support device can include one or more mechanical actuators, motors, linkages, kinematic mechanisms, etc. that can be transitioned between any suitable number of configurations to dynamically support and/or move a plate on which a user stands. While the fluid chambers 220 are described herein as being, for example, pneumatic devices (e.g., air driven), in other embodiments, a balance support device can include fluid chambers that are hydraulic devices (e.g., liquid driven).

Although various embodiments have been described as having particular features and/or combinations of components, other embodiments are possible having a combination of any features and/or components from any of embodiments as discussed above. For example, although the balance support system 200 is not described above with reference to FIGS. 2-8 as including a camera and/or video recording device, in other embodiments, the balance support system 200 can include a camera, video recording device, and/or any other suitable image capture device that can function similarly to the camera and/or video recording device described above with reference to the balance support system 100.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

What is claimed:

1. An apparatus, comprising:
   a plate configured to support a user standing on the plate;
   a plurality of fluid chambers, each fluid chamber from the plurality of fluid chambers configured to support at least a portion of the plate; and
   an electronic assembly in communication with at least one sensor, the electronic assembly configured to (1) receive a signal from the at least one sensor indicative of at least one of a pressure or a fill volume of each fluid chamber from the plurality of fluid chambers and (2) determine a tilt angle of the plate relative to a reference plane based on the at least one of the pressure or the fill volume of each fluid chamber from the plurality of fluid chambers, the electronic assembly configured to define a current coordinate along a plane based on the tilt angle of the plate relative to the reference plane and to send a signal indicative of an instruction to graphically represent data associated with the current coordinate on a display of an electronic device,
   in response to the current coordinate satisfying a criterion, the electronic assembly configured to send a signal operable to change the fill volume within at least one fluid chamber from the plurality of fluid chambers.

2. The apparatus of claim 1, wherein each fluid chamber from the plurality of fluid chambers is a pneumatic spring.

3. The apparatus of claim 2, further comprising:
   a control system including the at least one sensor, the control system is in electronic communication with the electronic assembly, the control system including a compressor in fluid communication with each fluid chamber from the plurality of the fluid chambers, the compressor configured to provide a flow of a compressed gas to at least one fluid chamber from the plurality of fluid chambers in response to a signal received from the electronic assembly.

4. The apparatus of claim 3, wherein the electronic assembly is configured to send a signal to the control system indicative of an instruction to perform at least one of a disconnecting of at least one fluid chamber from the plurality of fluid chambers, a measuring of a fluid pressure in at least one fluid chamber from the plurality of fluid chambers, or a changing of a fluid pressure in at least one fluid chamber from the plurality of fluid chambers.

5. The apparatus of claim 1, wherein the current coordinate satisfies the criterion when a difference between the current coordinate and a predetermined coordinate along the plane is within a predetermined threshold.

6. The apparatus of claim 1, wherein the plurality of fluid chambers includes four fluid chambers.

7. The apparatus of claim 1, wherein the at least one of the pressure or the fill volume of each fluid chamber from the plurality of fluid chambers is based at least in part on a force exerted by the user standing on the plate.

8. The apparatus of claim 1, wherein the at least one sensor includes at least a first sensor and a second sensor, the first sensor is configured to sense at least one of a pressure or a fill volume of at least one fluid chamber from the plurality of fluid chambers, the second sensor is configured to sense at least one of an orientation of the plate relative to the reference plane, a velocity associated with a change in orientation of the plate relative to the reference plane, or an acceleration associated with a change in orientation of the plate relative to the reference plane.

9. The apparatus of claim 1, wherein the electronic device is a first electronic device, the electronic assembly is in communication with at least the first electronic device and a second electronic device separate from the electronic assembly.

10. The apparatus of claim 9, wherein the second electronic device is a functional electrical stimulator donned by the user standing on the plate, an operating condition of the functional electrical stimulator being based at least in part on one or more signals received from the electronic assembly.

11. A method of using a balance support device having a plate, a plurality of fluid chambers configured to support the plate, and an electronic assembly including at least a processor, comprising:
    defining, at the processor, a predetermined coordinate along a plane, the predetermined coordinate based on a predetermined tilt angle of the plate relative to a reference plane;
    sending, from the processor and to a display, a signal indicative of an instruction to graphically represent data associated with the plane and the predetermined coordinate along the plane on the display;
    receiving, at the processor and from a sensor, a signal indicative of at least one of a pressure or a fill volume within each fluid chamber from the plurality of fluid chambers, the at least one of the pressure or the fill volume within each fluid chamber from the plurality of fluid chambers based at least in part on a force exerted by a user standing on the plate;
    defining, at the processor, a current tilt angle of the plate relative to the reference plane based on the at least one of the pressure or the fill volume within each fluid chamber from the plurality of fluid chambers;
    defining, at the processor, a coordinate along the plane based on the current tilt angle of the plate; and
    sending, from the processor to the display, a signal indicative of an instruction to graphically represent data associated with the coordinate and the data associated with the predetermined coordinate on the display.

12. The method of claim 11, wherein the balance support device includes a control system,
    the processor configured to send a signal to the control system indicative of an instruction to change a fill volume within at least one fluid chamber from the plurality of fluid chambers to move the plate relative to the reference plane.

13. The method of claim 11, wherein the coordinate along the plane substantially corresponds to a graphically represented position on the display.

14. The method of claim 11, further comprising:
sending, from the processor to the display, a signal indicative of an instruction to graphically represent an indication on the display when a difference between the coordinate and the predetermined coordinate is within a predetermined threshold.

15. The method of claim 11, wherein the predetermined coordinate is a first predetermined coordinate and the predetermined tilt angle is a first predetermined tilt angle, the method further comprising:
sending, from the processor to the display, a signal indicative of an instruction to graphically represent an indication on the display when a difference between the coordinate and the first predetermined coordinate is within a predetermined threshold; and
defining, at the processor, a second predetermined coordinate along the plane based on a second predetermined tilt angle, the second predetermined coordinate being different from the first predetermined coordinate and the second predetermined tilt angle being different from the first predetermined tilt angle.

16. A method of using a balance support device having a plate, a plurality of fluid chambers configured to support the plate, and an electronic assembly including at least a processor, comprising:
sending, from the processor and to a display, a signal indicative of an instruction to graphically represent data associated with a plane and a first target area along the plane on the display, the first target area having a first size and a first position along the plane;
receiving, at the processor and from a sensor, a signal indicative of at least one of a pressure or a fill volume within each fluid chamber from the plurality of fluid chambers, the at least one of the pressure or the fill volume within each fluid chamber from the plurality of fluid chambers based at least in part on a force exerted by a user standing on the plate;
defining, at the processor, a current coordinate along the plane, the current coordinate representing a tilt angle of the plate relative to a reference plane, the tilt angle determined based on the at least one of the pressure or the fill volume within each fluid chamber from the plurality of fluid chambers;
sending, from the processor to the display, a signal indicative of an instruction to graphically represent on the display (1) data associated with the plane and the current coordinate along the plane and (2) an indication when the current coordinate is disposed within the first target area; and
defining, at the processor, a second target area having a second size and a second position along the plane, the second size and the second position being different from the first size and the first position, respectively.

17. The method of claim 16, wherein
the balance support device includes a control system, the control system is in electronic communication with the electronic assembly and fluidic communication with each fluid chamber from the plurality of fluid chambers.

18. The method of claim 16, wherein the first target area encompasses a first plurality of coordinates along the plane, a difference between each coordinate from the first plurality of coordinates along the plane and a first predetermined coordinate along the plane being within a first predetermined threshold, and
the second target area encompasses a second plurality of coordinates along the plane, a difference between each coordinate from the second plurality of coordinates along the plane and a second predetermined coordinate along the plane being within a second predetermined threshold, the second predetermined threshold being different from the first predetermined threshold.

19. The method of claim 16, further comprising:
sending, from the processor to the display, a signal indicative of an instruction to graphically represent data associated with the plane and the second target area along the plane on the display.

20. The method of claim 16, further comprising:
sending, from the processor to the display, a signal indicative of an instruction to graphically represent data associated with the current coordinate and the data associated with the first target area on the display prior to the current coordinate satisfying the criterion.

* * * * *